(12) United States Patent
Yamane (10) Patent No.: US 8,491,468 B2
(45) Date of Patent: Jul. 23, 2013

(54) SUCTION SYRINGE AND ENDOSCOPE APPARATUS

(75) Inventor: Kenji Yamane, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 1014 days.

(21) Appl. No.: 12/372,457

(22) Filed: Feb. 17, 2009

(65) Prior Publication Data

US 2009/0209821 A1  Aug. 20, 2009

(30) Foreign Application Priority Data

Feb. 18, 2008 (JP) .................................. 2008-035846
Mar. 7, 2008 (JP) .................................. 2008-057342

(51) Int. Cl.
*A61B 1/12* (2006.01)
*A61M 5/00* (2006.01)

(52) U.S. Cl.
USPC ............. 600/158; 600/159; 600/432; 604/68; 604/135

(58) Field of Classification Search
USPC ............ 600/158, 568, 152, 159, 432; 604/68, 604/135
See application file for complete search history.

(56) References Cited

U.S. PATENT DOCUMENTS

| 3,815,481 A | * | 6/1974 | Pauliukonis | ..................... 92/86 |
| 4,549,554 A | * | 10/1985 | Markham | ..................... 600/566 |
| 4,572,210 A | * | 2/1986 | McKinnon | ..................... 600/578 |
| 4,664,128 A | * | 5/1987 | Lee | ..................... 600/566 |
| 4,667,691 A | * | 5/1987 | Sasa | ..................... 134/169 C |

FOREIGN PATENT DOCUMENTS

JP    2006-280537 A    10/2006

* cited by examiner

*Primary Examiner* — Alireza Nia
(74) *Attorney, Agent, or Firm* — Birch, Stewart, Kolasch & Birch, LLP (57) ABSTRACT

A tubular body has a vent hole $V_A$ and a suction opening. The piston body is in a state in which the inside of the tubular body in an enclosed space is divided into a front chamber and a rear chamber. The piston body includes piston portion which reciprocate in a position on its front end side from the suction opening, a shaft portion which supports this piston portion on its front end side and whose external diameter is smaller than the internal diameter of the tubular body and a pressing portion provided on a rear end side of this shaft portion. A vent passage is formed in the shaft portion so as to couple a vent hole $V_B$ of this pressing portion and a vent hole $V_C$ on its front end side of the shaft portion. Further, a spring is provided to return the pressed pressing portion to its original position.

1 Claim, 11 Drawing Sheets

SUCTION SYRINGE AND ENDOSCOPE APPARATUS

BACKGROUND OF THE INVENTION

The disclosure of Japanese Patent Applications No. 2008-035846, filed on Feb. 18, 2008, and No. 2008-057342, filed on Mar. 7, 2008, including its specification, claims and drawings, is incorporated herein by reference in its entirety.

FIELD OF THE INVENTION

The present invention relates to a configuration of a suction syringe capable of sucking fluid and a suction syringe for an endoscope which can be connected to a suction tube to suck fluid in an object to be observed in an endoscope and is portable.

DESCRIPTION OF THE RELATED ART

Figure 12:
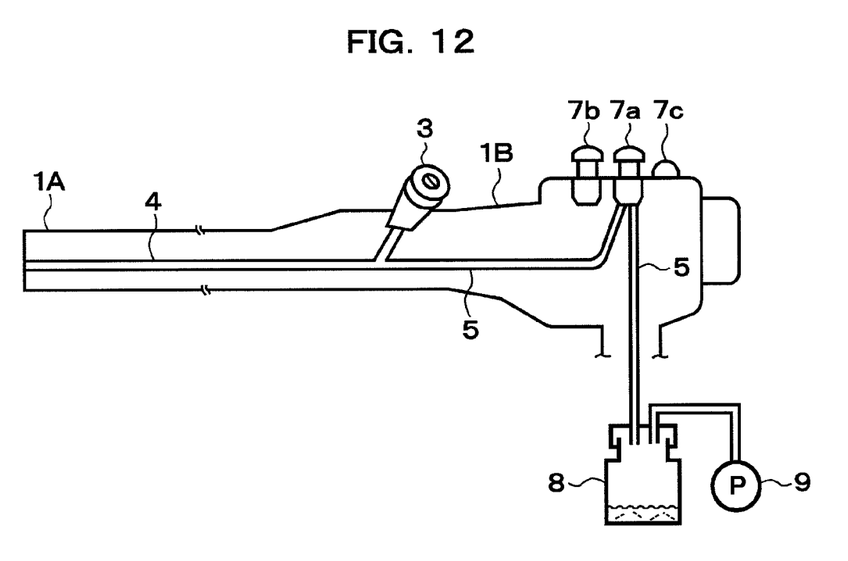
FIG. 12 is a drawing illustrating a configuration of a conventional endoscope apparatus.

FIG. 12 illustrates a configuration of a conventional endoscope apparatus. The endoscope (scope) has, for example, a front end portion 1A provided with a solid state image pickup element, an operation portion 1B provided through a curved portion, and the like. This operation portion 1B is provided with a forceps opening (treatment tool insertion channel inlet opening) 3 having a forceps plug. A treatment tool insertion channel 4 passing from the forceps opening 3 to the front surface of the front end portion 1A is disposed. The treatment tool insertion channel 4 connects to a suction tube 5 for sucking fluid (content) inside the object to be observed and the like. The treatment tool insertion channel 4 is configured to also function as the suction tube.

In addition, the operation portion 1B includes a suction button (mechanical or electrical) 7a, an air supply/water supply button 7b, a camera shutter release button 7c, and the like. The suction tube 5, for example, in the case of a mechanical suction tube, connects to a liquid storage tank 8 through a pipe connection portion in which the suction button 7a is disposed. The storage tank 8 connects to a suction pump 9.

According to such an endoscope apparatus, when the suction button 7a is operated, the suction action of the suction pump 9 causes to flow liquid (content) and the like inside the object to be observed through the treatment tool insertion channel 4 and the suction tube 5, and the liquid can be discharged to the storage tank 8. It should be noted that a treatment tool is introduced from the forceps opening 3 to the front end portion 1A, and various kinds of treatments can be performed inside the object to be observed.

However, as described above, the conventional endoscope apparatus requires the suction pump 9 for suction, and thus has a problem in that it is difficult to use the endoscope in a place other than a facility provided with the suction pump 9. In order to solve such a problem and obtain an endoscope excellent in portability, conventionally as disclosed in Japanese Patent Laid-Open No. 2006-280537, there has been a proposal to use a compressed gas cylinder and a nozzle unit to generate suction power by blowing a gas. However, even in this case, use of a compressed gas cylinder and a nozzle unit increases the size of the device and complicates its structure.

A portable endoscope apparatus (device) can be used in a various kinds of places other than a well-equipped facility, at bedside, and in emergency. In addition, a simplified configuration thereof leads to reduced costs. Therefore, a portable and simplified device for suction can provide a highly convenient endoscope apparatus.

Moreover, a widely used syringe provides suction by manually pulling a piston, but the suction is limited to the capacity of the cylinder tube and can be done only once. Therefore, an unlimited amount of fluid cannot be sucked in an easy and consecutive manner.

In view of the above problems, the present invention has been made, and an object of the present invention is to provide an endoscope apparatus capable of providing a simplified and portable device for suction leading to a portable and simplified suction syringe and endoscope apparatus capable of sucking an unlimited amount of fluid in an easy and consecutive manner.

SUMMARY OF THE INVENTION

In order to achieve the above object, the suction syringe of the present invention includes: a tubular body in which a suction opening is formed; a piston body which has a piston portion which reciprocates in close contact with a side surface inside the tubular body and whose reciprocating movement is used to suck fluid from the suction opening into a tubular body suction chamber, a shaft portion which supports this piston portion, and a pressing portion which is provided on a rear side of this shaft portion, wherein a shaft portion vent passage is formed in the shaft portion passing from a vent hole of this pressing portion to a vent hole on the suction chamber side of the shaft portion; and a biasing member which is disposed between the pressing portion of this piston body and the tubular body, and returns, to its original position, the piston body which has been moved forward.

The suction syringe is characterized in that moving the piston body forward or backward causes fluid to be sucked from the suction opening into the tubular body suction chamber, and the fluid inside this tubular body suction chamber is discharged outside through the shaft portion vent passage when the piston body is moved backward or forward.

Further, the suction syringe of another invention includes: a tubular body on whose front end portion a vent hole A is formed, on whose side surface portion a suction opening is formed and whose rear end portion is blocked; a piston body which has a piston portion which is in close contact with an inner surface of the tubular body in a state in which the inside of this tubular body is divided into a front chamber and a rear chamber, and reciprocates in a position from the suction opening to its front end side, a shaft portion which supports this piston portion (whose external diameter is smaller than the internal diameter of the tubular body), and a pressing portion which is provided on a rear side of this shaft portion, wherein a vent hole B is formed in this pressing portion, a vent passage communicatively connected to this vent hole B is formed in the shaft portion, and a vent hole C communicatively connected from the shaft portion vent passage to the tubular body rear chamber is formed in the shaft portion disposed in the tubular body rear chamber; and a spring which is disposed between the pressing portion of this piston body and the tubular body, and which returns the pressed piston body to its original position.

The suction syringe is characterized in that fluid is sucked from a suction opening of the tubular body by pressing the pressing portion with the vent hole B blocked.

In the above, a suction opening of the tubular body is pipe-connected to a fluid storage tank which is pipe-connected to a suction port of an endoscope, and the suction syringe according to a first aspect can be used as a suction device for the endoscope.

According to the above invention, for example, the front chamber and the rear chamber are formed in a space inside the tubular body enclosed by a discoid piston portion and a small diameter shaft portion. Then, when the pressing portion is pressed with a thumb or other finger, the piston body moves forward with the vent hole C being blocked, air inside the tubular body front chamber is pushed out of the vent hole A of the tubular body front end portion, and outside air is sucked into the tubular body rear chamber through the suction opening. That is, fluid in the pipe connected to the suction opening can be sucked. In the case of the endoscope apparatus, a storage tank is pipe-connected to the suction opening, and thus, liquid or the like inside the object to be observed is sucked from the suction port connected to this storage tank through the treatment tool insertion channel in the endoscope.

Subsequently, when the thumb or other finger is released from the pressing portion, air inside the tubular body rear chamber is discharged through the vent hole C, the shaft portion vent passage, and the vent hole B, while the piston body automatically moves backward by a biasing force of the spring and returns to its original position. Therefore, suction can be performed consecutively regardless of the capacity of the tubular body by repeatedly pressing the pressing portion.

Further, the suction syringe of another invention includes: a tubular body on whose front end side a suction opening is formed; a piston body which reciprocates in close contact with an inner surface of this tubular body and in which a first vent passage for discharging air inside the tubular body is formed; a first biasing member which is disposed between this piston body and the tubular body, and returns, to its original position, the piston body which has been moved forward; a pressing operation portion which has a pressing body which is coupled so as to reciprocate with respect to the piston body, and which functions as a pressing portion of the piston body, wherein a second vent passage is formed which is in an open state when this pressing body moves forward and is in a closed state when this pressing body moves backward, and when in this open state, air inside the tubular body is discharged outside from the first vent passage; and a second biasing member which is disposed between the pressing body of this pressing operation portion and the piston body, and returns, to its original position, the pressing body which has been moved forward by a finger pressure.

The suction syringe is characterized in that when the pressing body of the pressing operation portion is pressed, the piston body is moved forward while air inside the tubular body is discharged outside through the opened second vent passage and the first vent passage; and when the finger pressure on the pressing body is released, the second vent passage is caused to be in a closed state, fluid is sucked from a suction opening while the piston body is moved back to its original position by the first biasing member.

In the above suction syringe, a suction opening of the tubular body is pipe-connected to a fluid storage tank which is pipe-connected to a suction port of an endoscope, and the suction syringe can used as a suction device for the endoscope.

According to the above invention, when the pressing body of the pressing operation portion is pressed with a thumb or other finger against the second biasing member to move the pressing body forward (or pressed to the first position), the second vent passage inside the pressing operation portion is in an open state. Subsequently, when the piston body is pressed with the pressing body against the first biasing member forward (or pressed to the second position), the piston body moves forward to the front end side, while air inside the tubular body is discharged outside through the first vent passage and the second vent passage. Afterward, when the finger pressure is released, the second biasing member causes the pressing body to move backward. Then, the second vent passage inside the pressing operation portion is in a closed state, thereby stopping air from being discharged from the first vent passage and the second vent passage. At the same time, the first biasing member causes the piston body to move backward. As a result, outside air is sucked from the suction opening. That is, fluid in a portion in which the suction opening is disposed can be sucked.

Moreover, at the time of the above pressing operation, air inside the tubular body is automatically discharged outside. Therefore, suction can be performed consecutively regardless of the capacity of the tubular body by repeatedly pressing the pressing portion.

Further, when the suction syringe is used in an endoscope apparatus, the storage tank is connected to the suction opening through a connecting tube, causing the inside of the storage tank to be in a pressure-reduced state. Therefore, liquid or the like in the object to be observed is sucked through the treatment tool insertion channel in the endoscope, the suction tube, and the suction port, and this liquid or the like is stored in the storage tank.

Further, the endoscope apparatus of another invention is characterized in that the above configured suction syringe is used as a suction device of an endoscope apparatus whose suction tube is open/close controlled by a suction operation portion having a suction tube open/close mechanism; and the suction syringe is used such that a fluid storage tank is pipe-connected to a suction port coupled to the suction operation portion and the suction opening of the tubular body is pipe-connected to this fluid storage tank; and when the piston body moves forward, suction is performed by operating the suction operation portion.

According to such an invention, when the piston body is in a pressed state after the suction opening is connected to the suction port, a necessary amount of fluid can be sucked by operating an endoscope suction button in an appropriate and easy manner.

The suction syringe of the present invention has an advantage in that an unlimited amount of fluid can be sucked in an easy and consecutive manner by repeating a pressing operation of the pressing portion.

Further, according to the suction syringe for an endoscope or the endoscope apparatus, a portable and simplified device for suction leading to a portable and simplified endoscope apparatus is enabled. Therefore, the endoscope can be easily used in a various kinds of places other than a well-equipped facility, at bedside, and in emergency, which has an advantage capable of providing a highly convenient endoscope apparatus.

DETAILED DESCRIPTION OF THE PREFERRED EMBODIMENTS

First Embodiment

Figure 1A:
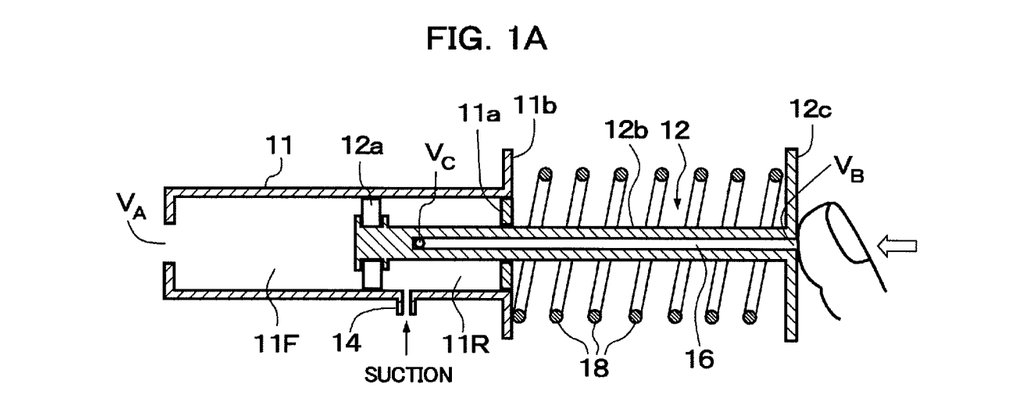
FIG. 1A is a sectional view illustrating a configuration of a suction syringe, when not operated, in accordance with a first embodiment of the present invention.
Figure 1B:
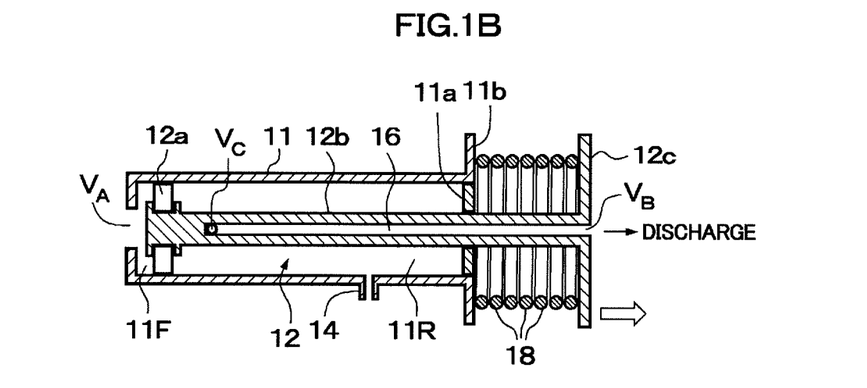
FIG. 1B is a sectional view of the suction syringe, when pressed, of FIG. 1A.

FIGS. 1A and 1B illustrate a suction syringe in accordance with the first embodiment; and FIGS. 2A and 2B to FIG. 4 illustrate a configuration in the case of the suction syringe of the first embodiment applied to an endoscope apparatus. As shown in FIGS. 1A and 1B, the suction syringe has a cylindrical tubular body 11 and a piston body (slider) 12. In the tubular body 11, its rear end is blocked by a circular blocking (airtight) plate 11a, a vent hole $V_A$ is provided on its front surface (tubular body front chamber 11F), and a suction opening 14 is provided on a side surface (tubular body rear chamber 11R) on the rear side from the center portion. It should be noted that the vent hole $V_A$ may be opened on a side surface of the front end portion of the tubular body.

On the one hand, the piston body 12 includes a discoid piston portion (sliding portion) 12a which slides (reciprocates) in close contact with an inner surface of the tubular body 11 and has a predetermined thickness to divide the tubular body into the front chamber 11F and the rear chamber 11R, a cylindrical rod-shaped shaft portion 12b which supports the piston portion 12a and whose external diameter is smaller than the internal diameter of the tubular body 11, and a discoid pressing portion 12c which is disposed at a rear side of the shaft portion 12b so as to move back and forth when pressed with a thumb or other finger.

Moreover, a vent hole $V_B$ is formed in a middle portion of the pressing portion 12c, and a shaft portion vent passage (tube path) 16 is formed in the middle of the shaft portion 12b in the radial direction thereof so as to be communicatively connected to the vent hole $V_B$. A vent hole $V_C$ communicatively connected to tubular body rear chamber 11R from the vent passage 16 is formed on the front end side of the shaft portion 12b (inside the tubular body rear chamber 11R). Further, a spring 18 urging the pressed pressing portion 12c in a direction to its original position is provided (in a state engaged with each other) between a flange portion 11b on the rear side of the tubular body 11 and the pressing portion 12c of the piston body 12.

According to such a suction syringe, in a basic (not operated) state shown in FIG. 1A, when the pressing portion 12c is pressed by a thumb or other finger plugging the vent hole $V_B$ (against the spring 18), air inside the front chamber 11F of the tubular body 11 can be discharged from the vent hole $V_A$, while the rear chamber 11R increases in volume, thereby allowing outside air to be sucked into the rear chamber 11R through the suction opening 14. Therefore, when the front end opening of a tube connected to this suction opening 14 is disposed in liquid to be sucked, the liquid can be sucked therefrom.

Then, in a state shown in FIG. 1B, when the finger pressure on the pressing portion 12c is released, the vent hole $V_B$ is opened and the piston body 12 is urged to this rear side by the spring 18. Then, air inside the rear chamber 11R is discharged from the vent hole $V_B$ through the vent hole $V_C$ and the shaft portion vent passage 16. Then, the piston body 12 automatically returns to its original basic state shown in FIG. 1A. Accordingly, liquid can be sucked several times in a row by repeatedly pressing the pressing portion 12c.

Figures 2A, 2B:
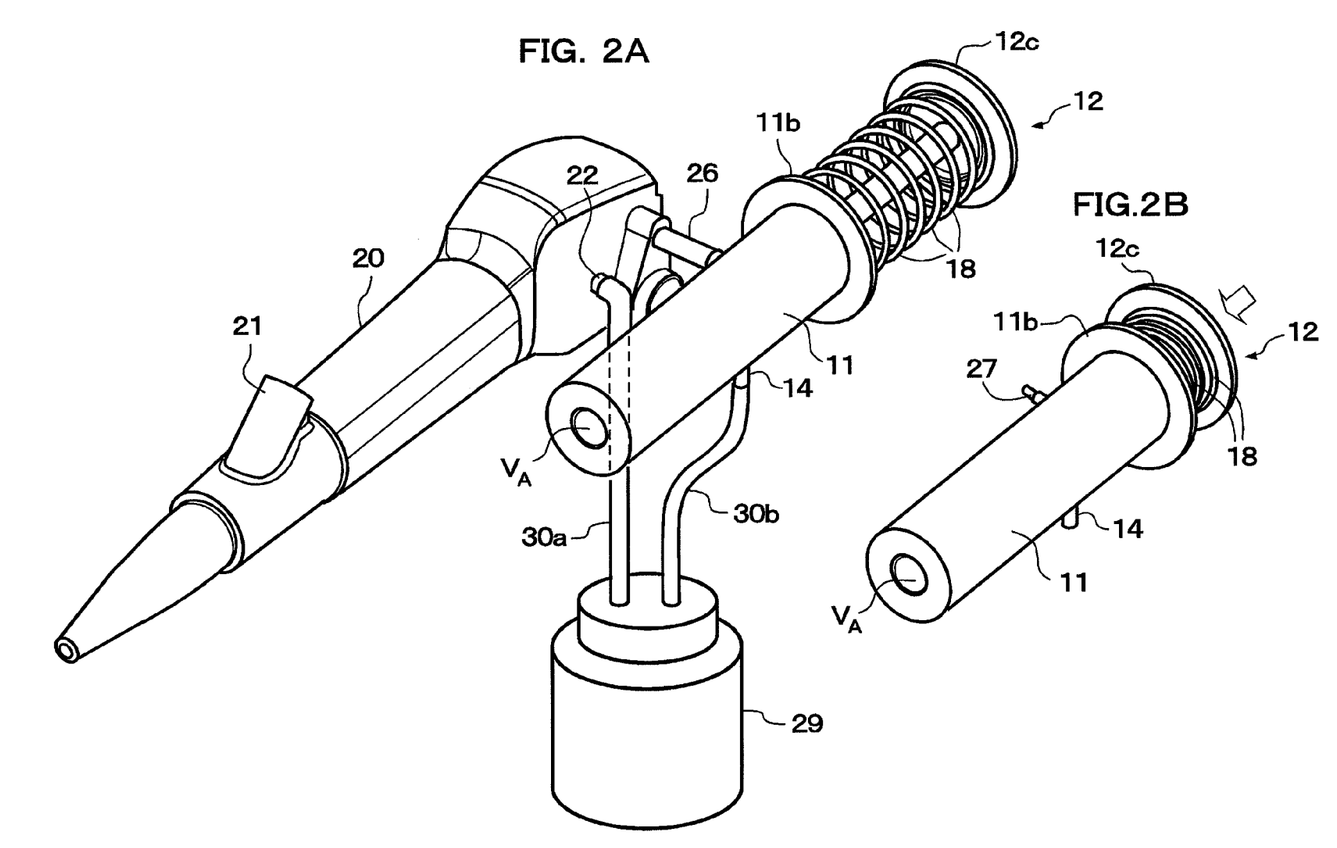
FIG. 2A is a perspective view illustrating a configuration of the suction syringe for an endoscope, when not operated, in accordance with the first embodiment.
FIG. 2B is a perspective view of the suction syringe, when pressed, of FIG. 2A.

FIGS. 2A and 2B to FIG. 4 illustrate a configuration of the suction syringe connected to an endoscope. As shown in FIG. 2A, a forceps opening 21 of the treatment tool insertion channel and a suction port (suction tube connection opening) 22 are provided in the endoscope operation portion (structure) 20. A suction tube 24 is disposed in the operation portion so as to be communicatively connected to the suction port 22 and to the treatment tool insertion channel. On the other hand, for example, a syringe fixing portion (attachment portion) 26 having a circular hole with a predetermined depth is provided on a side surface of the operation portion 20 or the like. A circular rod-shaped projection portion 27 fit into a circular hole of the fixing portion 26 is provided on a side surface of the syringe 11. The syringe 11 can be installed and fixed to a side surface of the operation portion 20 by fitting this projection portion 27 into the fixing portion 26.

Moreover, a tank 29 storing sucked fluid is provided in the endoscope apparatus. This tank 29 connects to the suction port 22 through a connecting tube 30a and also connects to the suction opening 14 of the syringe 11 through a connecting tube 30b.

Figure 3:
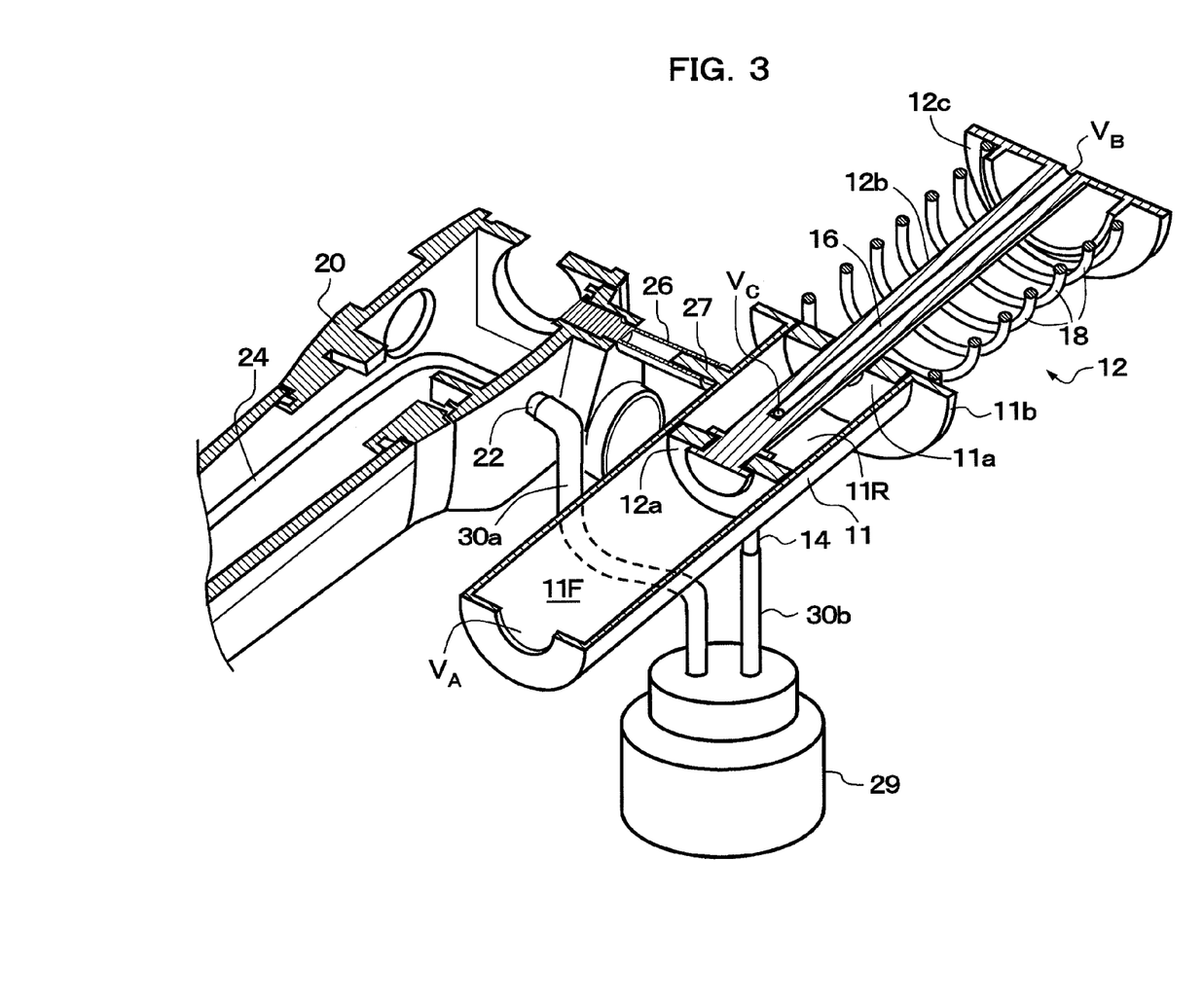
FIG. 3 is a perspective sectional view illustrating a configuration of the suction syringe for an endoscope, when not operated, in accordance with the first embodiment.
Figure 4:
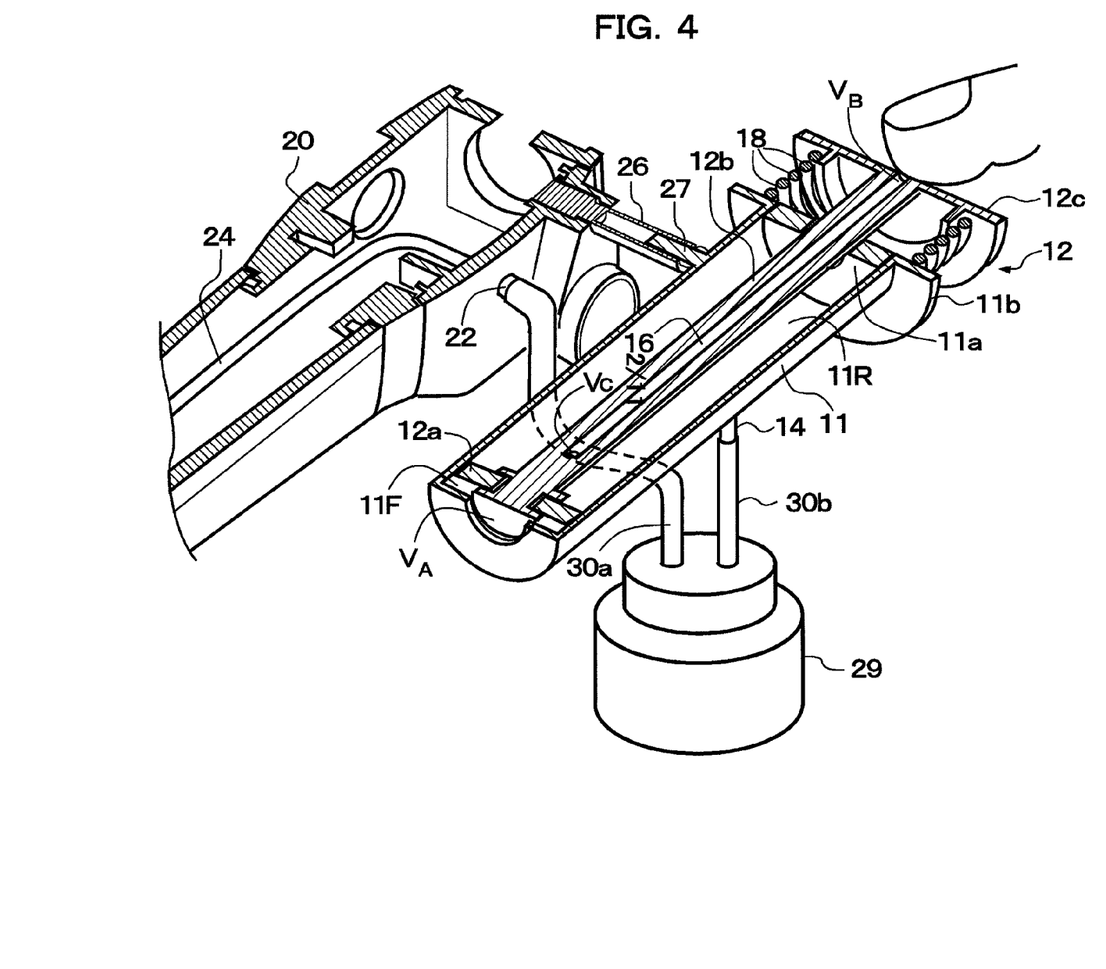
FIG. 4 is a perspective sectional view illustrating a configuration of the suction syringe for an endoscope, when pressed, in accordance with the first embodiment.

According to such an endoscope apparatus, in a basic state shown in FIG. 3, when the pressing portion 12c is pressed by a thumb or other finger plugging the vent hole $V_B$ (against the spring 18) as shown in FIG. 4, air inside the front chamber 11F of the tubular body 11 is discharged from the vent hole $V_A$, while the rear chamber 11R increases in volume, thereby allowing air inside the tank 29 to be sucked into the rear chamber 11R through the suction opening 14. As a result, when the pressure inside the tank 29 is reduced, fluid (content and the like) inside the object to be observed is sucked from the front end portion of the endoscope through the suction tube 24 and stored in the tank 29.

Then, in a state shown in FIG. 4, when the thumb or other finger is released from the pressing portion 12c to release the finger pressure, the vent hole $V_B$ is opened and the piston body 12 is urged to the rear side by the spring 18. Then, air inside the rear chamber 11R is discharged outside from the vent hole $V_C$ through the shaft portion vent passage 16 and the vent hole $V_B$, and the piston body 12 automatically returns to its original basic state shown in FIG. 3. Accordingly, an unlimited amount of liquid can be sucked several times in a row by repeatedly pressing the pressing portion 12c.

According to the present embodiment, the piston body 12 stops at a basic position corresponding to the length of the spring 18 as shown in FIG. 1A or FIG. 3, but a stopper mechanism for ensuring a reliable and stable stop operation can be provided between the tubular body 11 and the shaft portion 12b.

Second Embodiment

Figure 5A:
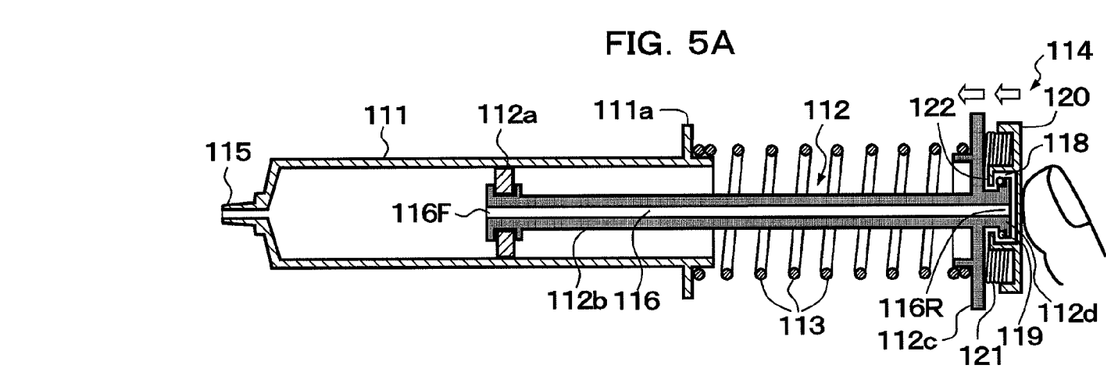
FIG. 5A is a sectional view illustrating a configuration of a suction syringe, when not operated, in accordance with a second embodiment of the present invention.
Figure 5B:
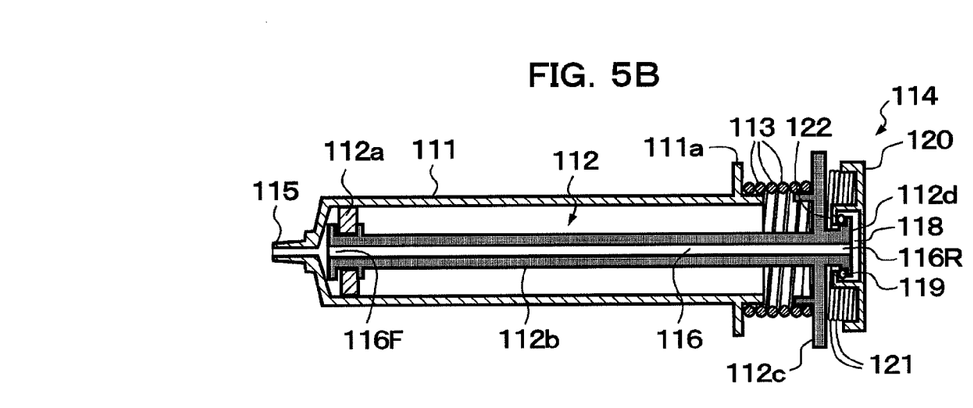
FIG. 5B is a sectional view of the suction syringe, when pressed, of FIG. 5A.

FIGS. 5A and 5B to FIGS. 7A and 7B illustrate a suction syringe in accordance with a second embodiment. FIGS. 8 to FIG. 11 illustrate a configuration in the case of the suction syringe of the second embodiment applied to an endoscope apparatus. With reference to FIG. 5A and FIG. 5B, the suction syringe includes a circular tubular body 111, a piston body (slider) 112, a first spring 113, and a pressing operation portion 114. A suction opening (hole) 115 is provided on the front end portion of the tubular body 111. On the one hand, the piston body 112 includes a discoid piston portion (sliding portion) 112a which slides (reciprocates) in close contact with an inner surface of the tubular body 111 and has a predetermined thickness, and a cylindrical rod-shaped shaft portion 112b which supports this piston portion 112a. A first vent passage (tube path) 116 passing from the front end opening 116F of the shaft portion 112b to the rear end opening 116R is formed in the middle of the shaft portion 112b in the radial direction thereof.

Figure 6A:
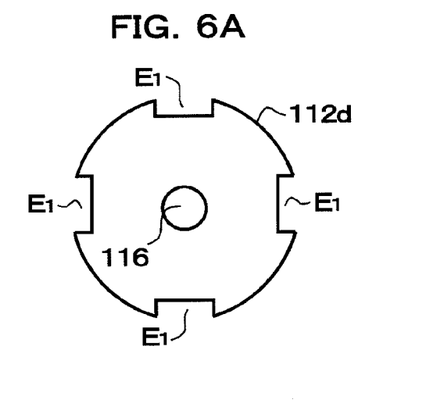
FIG. 6A is a drawing of a small disk portion of the pressing operation portion of the suction syringe in accordance with the second embodiment viewed from its rear end side.
Figure 6B:
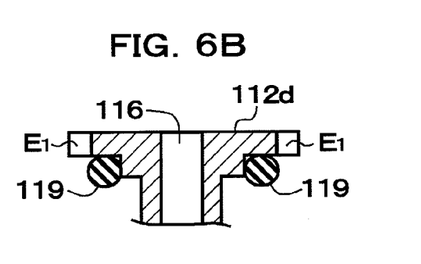
FIG. 6B is a sectional view of the small disk portion of FIG. 6A.
Figure 7A:
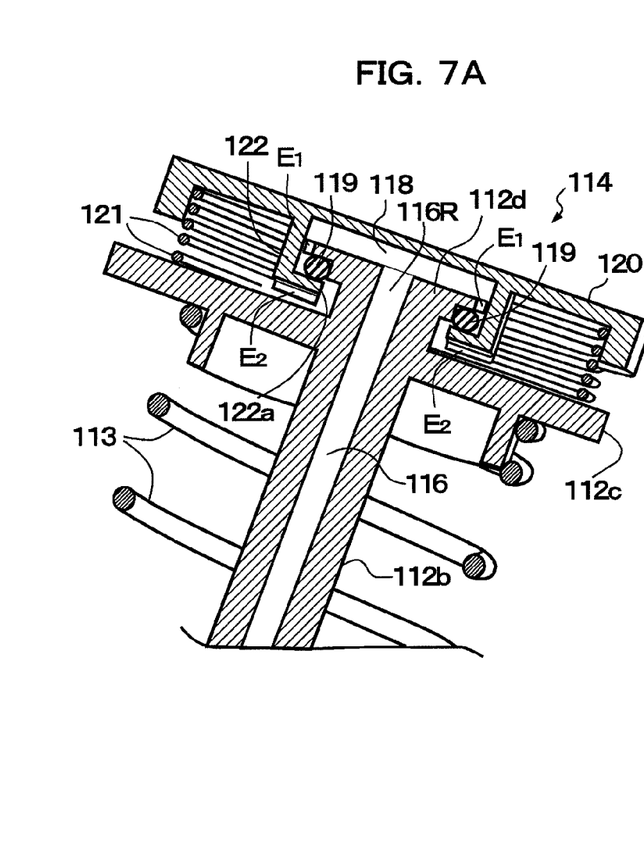
FIG. 7A is a sectional view showing an enlarged view of the pressing operation portion of the suction syringe, when not operated, of the second embodiment.
Figure 7B:
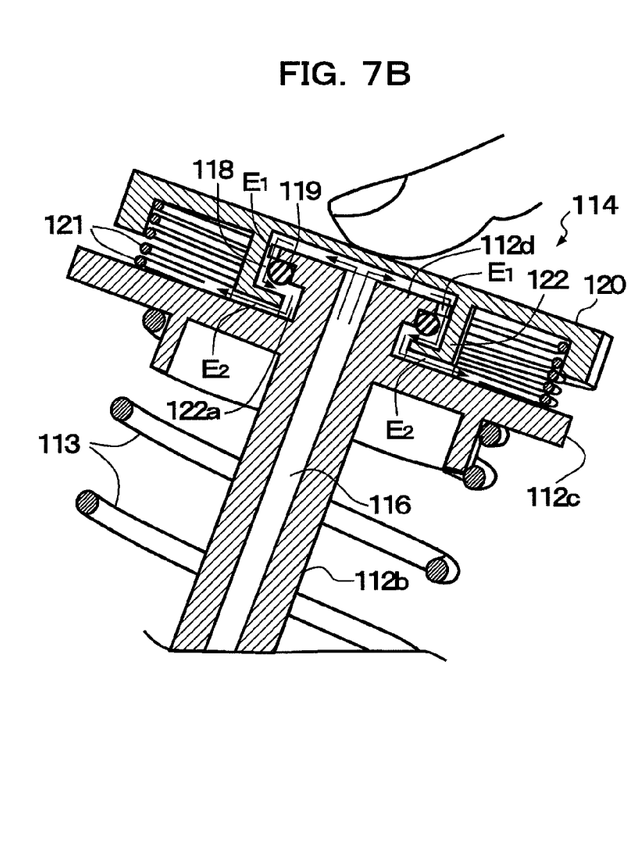
FIG. 7B is a sectional view of the suction syringe, when pressed, of FIG. 7A.

In addition, the pressing operation portion 114 is integrally provided in a rear end portion of this shaft portion 112b. As shown in FIGS. 7A and 7B, this pressing operation portion 114 includes a support disk portion 112c on the piston body 112 side, a small disk portion 112d for forming a second vent passage 118, an O-ring 119, a circular coronal pressing body 120, and a second spring (spring) 121. That is, the O-ring 119 is attached to a stepped portion formed on the underside (front side) of the small disk portion 112d. As shown in FIGS. 6A and 6B, a vent channel $E_1$ constituting part of the second vent passage 118 is notched and formed into a plurality of (e.g., four) positions on an outer periphery of the small disk portion 112d.

Figure 6C:
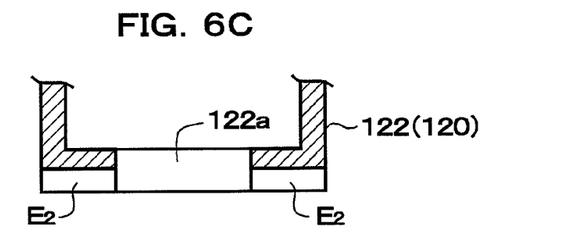
FIG. 6C is a sectional view of the surrounding body of the pressing operation portion of the second embodiment.
Figure 6D:
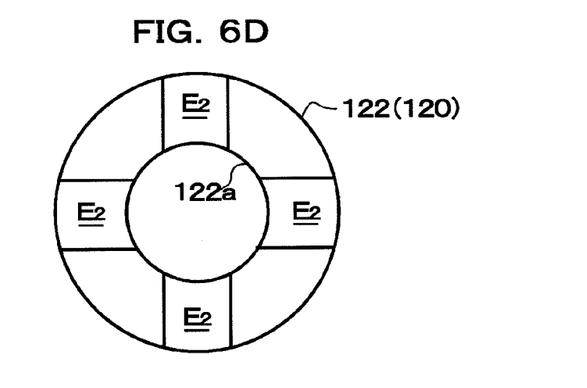
FIG. 6D is a drawing of the surrounding body of FIG. 6C viewed from its front end side.

The coronal pressing body 120 has a surrounding body 122 in the center of the underside (front side) thereof. The surrounding body 122 is a circular dish-shaped body forming a circular cavity whose radius is a little smaller than that of the small disk portion 112d, and a circular opening 122a is opened in its center. The small disk portion 112d is disposed in this surrounding body 122. In addition, as shown in FIGS. 6C and 6D, this surrounding body 122 has a vent channel $E_2$ formed in a plurality of (e.g., four) positions in the circumferential direction of the bottom portion (front side) thereof from the circular opening 122a to the outer periphery side. Then, the second spring 121 is disposed between the coronal pressing body 120 and the support disk portion 112c so as to urge this pressing body 120 in the rear end direction.

According to such a configuration of the pressing operation portion 114, as shown in FIG. 7A, when the operation of the pressing body 120 is released, the second spring 121 is urged to move the pressing body 120 to its rear end side and the inner surface (dish-shaped bottom portion) of the surrounding body 122 comes in close contact with the O-ring 119 on the underside of small disk portion 112d. Therefore, the second vent passage 118 is in a closed state. On the other hand, as shown in FIG. 7B, when the pressing body 120 is pressed, the pressing body 120 moves to the piston body side of its front end side, and the inner surface of the surrounding body 122 moves away from the O-ring 119. Therefore, the second vent passage 118 communicatively connected from the first vent passage 116 is in an open state. That is, the second vent passage 118 is composed of a space inside the surrounding body 122 communicatively connected the first vent passage 116, a vent channel $E_1$, a circular opening 122a and a vent channel $E_2$. Air is discharged outside from this vent channel $E_2$.

Further, the first spring 113 is disposed (in a state engaged with each other) between a flange portion 111a on the rear side of the tubular body 111 and the support disk portion 112c of the pressing operation portion 114, thereby allowing the pressed piston body 112 to return (move backward) to its original position.

According to such a suction syringe, in a basic (not operated) state shown in FIG. 5A, when the pressing body 120 (pressing operation portion 114) is pressed with a thumb or other finger against a biasing force of the second spring 121 (or pressed to the first position) as shown in FIG. 7B, the pressing body 120 moves to the piston body side. Then, the inner surface of the surrounding body 122 moves away from the O-ring 119 and the second vent passage 118 composed of the space inside the surrounding body 122, the vent channel $E_1$, the circular opening 122a and the vent channel $E_2$ is in an open state. Subsequently, when the pressing body 120 is pressed against a biasing force of the first spring 113 (or pressed to the second position), air inside the tubular body 111 passes through the first vent passage 116 (from the front end opening 116F to the rear end opening 116R), and is discharged outside through the second vent passage 118. Thereby, the piston body 112 can be moved forward to the front end position without discharging air from the suction opening 115, and then is in a state shown in FIG. 5B.

In a state shown in FIG. 5B, when the finger pressure on the pressing body 120 is released, the inner surface of the surrounding body 122 comes in close contact with the O-ring 119 as shown in FIG. 7A and the second vent passage 118 is in a closed state. Then, air inside the tubular body 111 is blocked from being discharged outside through the first vent passage 116, and outside air is sucked into the tubular body 111 through the suction opening 115. Therefore, when the suction opening 115 or the front end opening of a tube connected to this is disposed in liquid to be sucked, the liquid can be sucked therefrom.

The two-step pressing operation with the pressing body 120 can be repeated after the suction, an unlimited amount of liquid can be sucked by repeatedly pressing several times in a row.

Figure 8:
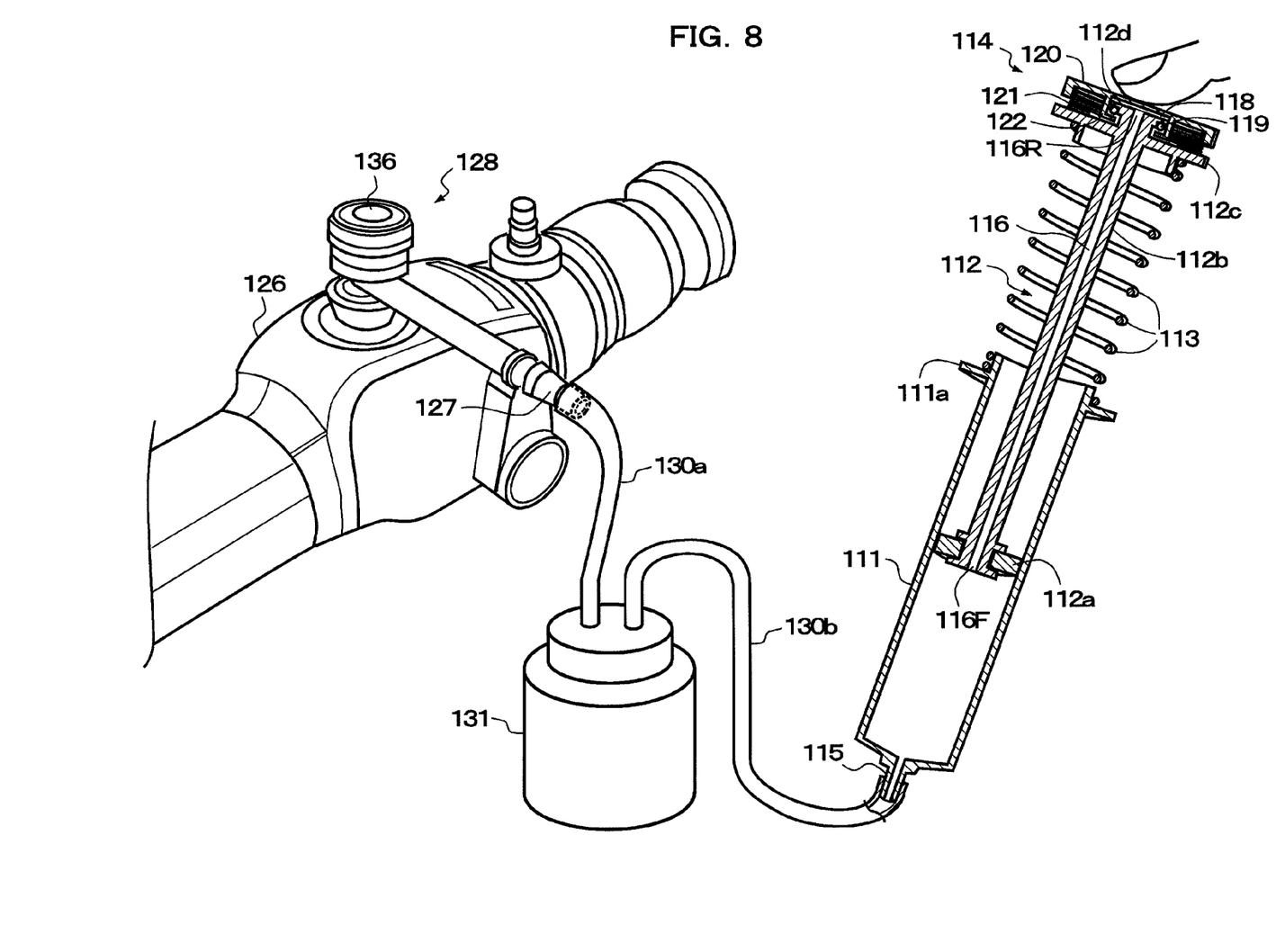
FIG. 8 is a perspective (partial sectional) view of a configuration of the endoscope apparatus using the suction syringe in accordance with the second embodiment illustrating a state where it is not operated.
Figure 9:
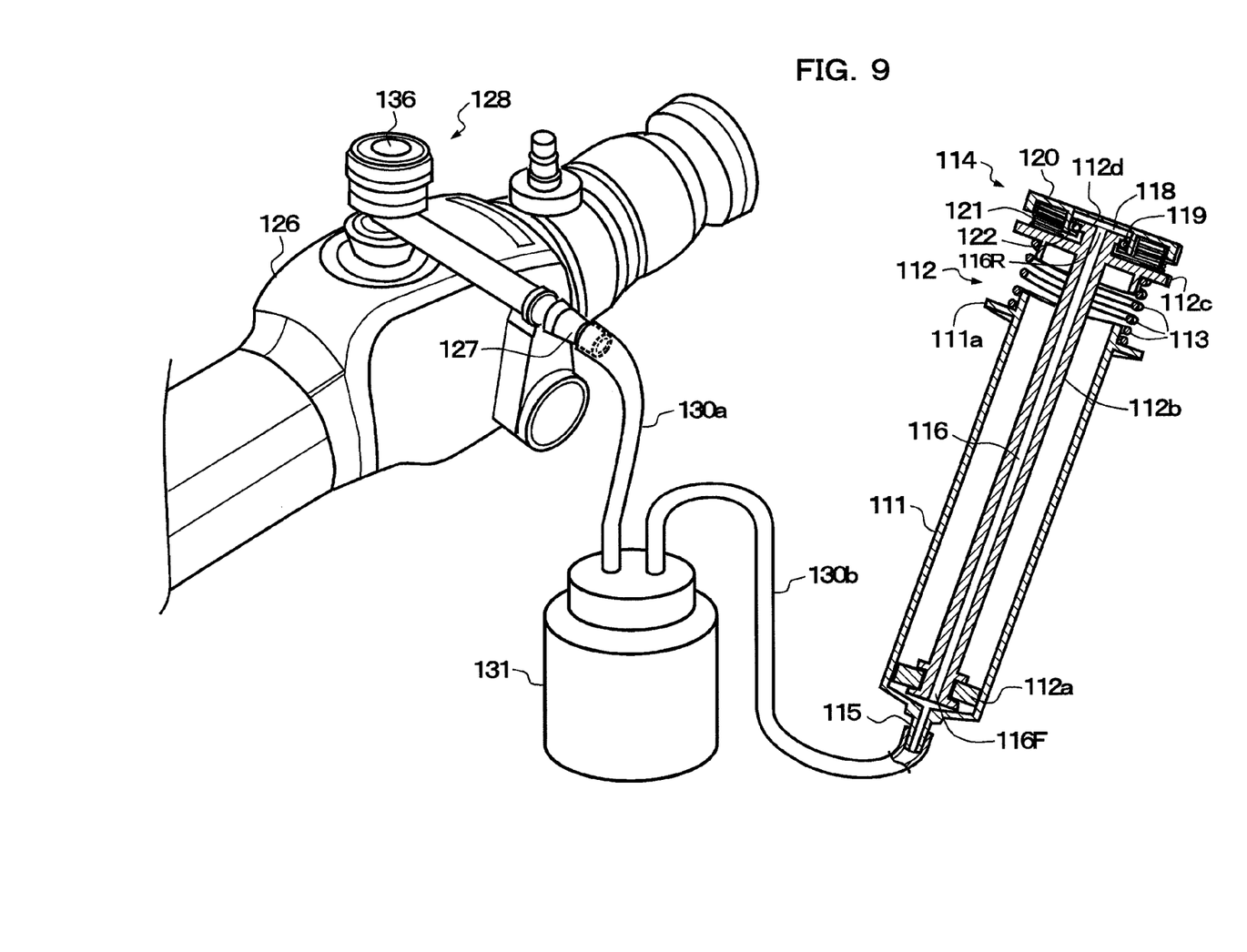
FIG. 9 is a perspective (partial sectional) view of a configuration of the endoscope apparatus using the suction syringe in accordance with the second embodiment illustrating a state where it is pressed.

FIG. 8 and FIG. 9 illustrate a configuration of the suction syringe applied to an endoscope apparatus. As shown in FIG. 8 and FIG. 9, the endoscope operation portion 126 includes a suction operation portion 128, for example, provided with a suction port (suction tube connection opening) 127. This suction port 127 of the suction operation portion 128 connects to (one of connection openings of) a tank 131 storing liquid to be sucked through the connecting tube 130a. In addition, (the other of connection openings of) the tank 131 connects the suction opening 115 of the suction syringe through the connecting tube 130b.

Figure 10:
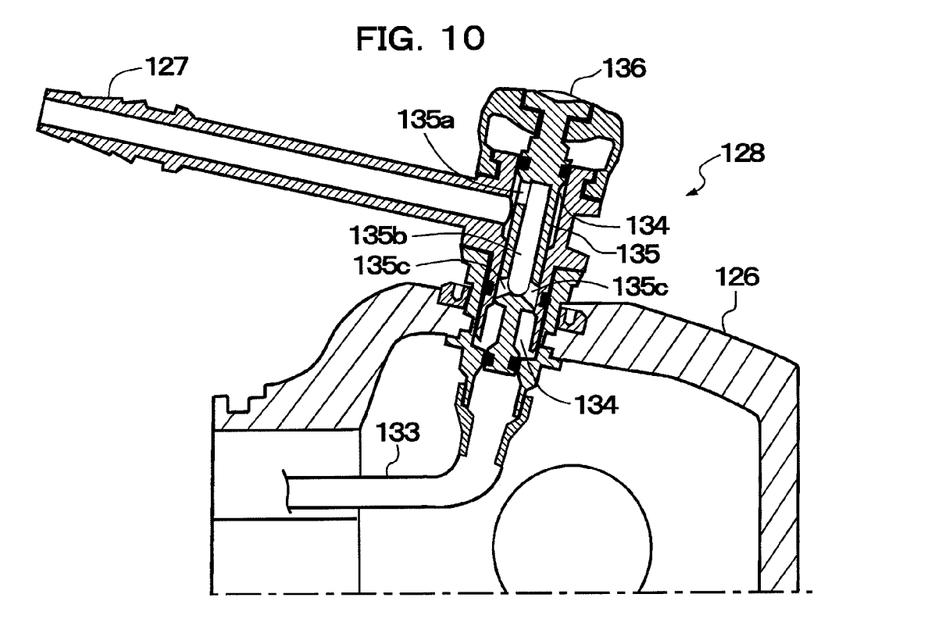
FIG. 10 is a sectional view of a configuration of a suction operation portion of the endoscope apparatus in accordance with the second embodiment illustrating a state where it is not operated.
Figure 11:
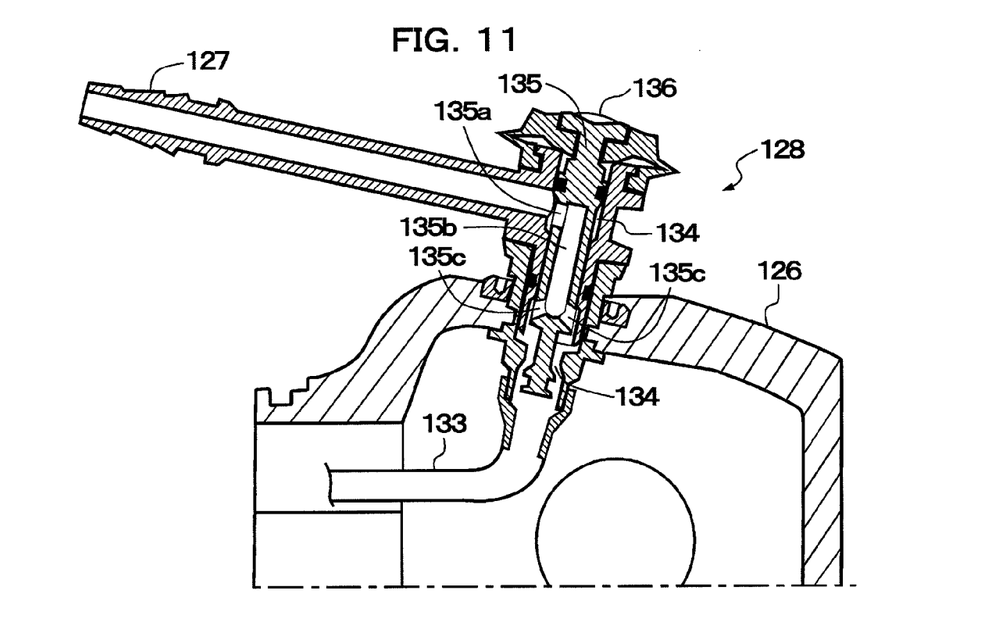
FIG. 11 is a sectional view of a configuration of the suction operation portion of the endoscope apparatus in accordance with the second embodiment illustrating a state where it is pressed.

FIG. 10 and FIG. 11 illustrate an internal configuration of the suction operation portion 128 provided in the endoscope operation portion 126. This suction operation portion 128 includes a central passage 134 which is coupled to a tube path of the suction port 127 and is coupled to a suction tube 133 in the endoscope; a piston member 135 configured to be so as to move up and down inside this central passage 134; and a suction button 136 disposed in an upper portion of this piston member 135 to urge an elastic body (rubber member) of the piston member 135 to the upper side. The piston member 135 includes an upper side opening 135a, an internal passage 135b, and an underside opening 135c, which constitute a suction tube open/close mechanism.

According to the suction operation portion 128, as shown in FIG. 10, the underside opening 135c of the piston member 135 is blocked by the central passage 134 and the most underside portion (outer periphery) of the piston member 135 comes in close contact with the underside portion (inner surface) of the central passage 133, thereby closing the suction tube 133. As shown in FIG. 11, when the suction button 136 is pressed, the piston member 135 moves to the underside. Then, the underside opening 135c of the piston member 135 and the most underside portion move away from the central passage 134, thereby opening the suction tube 133.

According to such an endoscope apparatus, in the suction syringe, in a basic state shown in FIG. 8, when the pressing body 120 is pressed to the first position with a thumb or other finger, as described in FIG. 7B, the pressing body 120 moves to the piston body side, and the inner surface of the surrounding body 122 moves away from the O-ring 119. Then, the second vent passage 118 composed of the space inside the surrounding body 122, the vent channel $E_1$, the circular opening 122a, and the vent channel $E_2$ is in an open state. Subsequently, when the pressing body 120 is pressed to the second position, air inside the tubular body 111 is discharged outside through the first vent passage 116 and the second vent passage 118. Then, as shown in FIG. 9, the piston body 112 moves to the front end side position and is in a suckable state. That is, a suction power of the suction syringe causes the inside of the tank 131 to be pressure-reduced.

Then, in the endoscope operation portion 126, when the suction button 136 of the suction operation portion 128 is pressed in a state of FIG. 10, the piston member 135 moves to the underside as shown in FIG. 11, and the suction tube 133 is in an open state. Therefore, the suction syringe generates a suction power, causing the inside of the tank 131 to be pressure-reduced. Thereby, fluid (content and the like) inside the object to be observed passes through the treatment tool insertion channel of the front end portion of the endoscope, the suction tube 133, the central passage 134, the underside opening 135c, the internal passage 135b, and the upper side opening 135a, and further is sucked through the suction port 127 and the connecting tube 130a and stored into the tank 131.

Such an operation of the suction operation portion 128 has an advantage capable of sucking a necessary and small amount of fluid in an appropriate and easy manner. Moreover, when the piston body 112 of the suction syringe completely returns to its original position, an unlimited amount of fluid can be sucked by repeating a pressing operation of the piston body 112 by the pressing operation portion 114.

It should be noted that, according to the present embodiment, the piston body 112 stops at a basic position corresponding to the length of the first spring 113 as shown in FIG. 5A or FIG. 7A, but a stopper mechanism for ensuring a reliable and stable stop operation can be provided between the tubular body 111 and the shaft portion 112b.

DESCRIPTION OF SYMBOLS 5, 24, 133 suction tube
11, 111 tubular body
11F front chamber
11R rear chamber
12, 112 piston body
12, 112a piston portion (sliding portion)
12b, 112b shaft portion
12c, 112c pressing portion
12d small disk portion
14, 115 suction opening
16 shaft portion vent passage
18, 113 spring
22, 127 suction port
26 fixing portion
27 projection portion
29, 131 storage tank
114 pressing operation portion
115 suction opening
116 first vent passage
118 second vent passage
119 O-ring
120 pressing body
121 second spring
122 surrounding body
128 suction operation portion
134 central passage
135 piston member
136 suction button
$V_A$ vent hole A
$V_B$ vent hole B
$V_C$ vent hole C
$E_1$, $E_2$ vent channel

What is claimed is:

1. A suction syringe comprising:
a tubular body in which a suction opening is formed;
a piston body comprising
a piston portion which reciprocates in close contact with a side surface in the tubular body and whose reciprocating movement is used to suck fluid from the suction opening into a tubular body suction chamber;
a shaft portion which supports the piston portion;
a pressing portion which is provided on a rear side of the shaft portion;
a shaft portion vent passage formed in the shaft portion;
a first vent hole formed in the pressing portion communicating with the vent passage; and
a second vent hole in a side of the shaft portion; and
a biasing member which is disposed between the pressing portion of the piston body and the tubular body, and returns the piston body to an original position after the piston body has been moved forward,
wherein moving the piston body forward causes fluid to be sucked from the suction opening into the tubular body, and fluid inside the tubular body is discharged outside through the shaft portion vent passage when the piston body is moved backward,
wherein a suction opening of the tubular body is pipe-connected to a fluid storage tank which is pipe-connected to a suction port of an endoscope, and the suction syringe is used as a suction device for the endoscope,
wherein the piston portion divides the tubular body into a front chamber and a rear chamber, wherein a third vent hole is formed on the tubular body at a front end of the tubular body so as to communicate with the front chamber, wherein the second vent hole and the suction opening communicate with the rear chamber, and wherein fluid is sucked through the suction opening into the rear chamber by moving the piston body forward with the first vent hole blocked.

* * * * *